US010813534B2

(12) United States Patent
Yamaya

(10) Patent No.: US 10,813,534 B2
(45) Date of Patent: Oct. 27, 2020

(54) DISTAL-END COVER, INSERTION DEVICE ATTACHED WITH DISTAL-END COVER, AND ENDOSCOPE INCLUDING INSERTION DEVICE

(71) Applicant: OLYMPUS CORPORATION, Tokyo (JP)

(72) Inventor: Koji Yamaya, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 420 days.

(21) Appl. No.: 15/855,171

(22) Filed: Dec. 27, 2017

(65) Prior Publication Data

US 2018/0116491 A1 May 3, 2018

Related U.S. Application Data

(63) Continuation of application No. PCT/JP2016/067411, filed on Jun. 10, 2016.

(30) Foreign Application Priority Data

Jun. 30, 2015 (JP) .................................. 2015-131295

(51) Int. Cl.
*A61B 1/00* (2006.01)
*A61B 1/018* (2006.01)
(Continued)

(52) U.S. Cl.
CPC ........ *A61B 1/00135* (2013.01); *A61B 1/0008* (2013.01); *A61B 1/00098* (2013.01);
(Continued)

(58) Field of Classification Search
CPC ............ A61B 1/00135; A61B 1/00089; A61B 1/00098; A61B 1/000101; A61B 1/00128;
(Continued)

(56) References Cited

U.S. PATENT DOCUMENTS 5,662,588 A * 9/1997 Iida ..................... A61B 1/00091
600/121
5,860,913 A * 1/1999 Yamaya ............. A61B 1/00091
600/121
(Continued)

FOREIGN PATENT DOCUMENTS

JP H07323001 A 12/1995
JP H08243071 A 9/1996
(Continued)

OTHER PUBLICATIONS

International Search Report dated Aug. 23, 2016 issued in PCT/JP2016/067411.
(Continued)

*Primary Examiner* — John P Leubecker
(74) *Attorney, Agent, or Firm* — Scully, Scott, Murphy & Presser, P.C.

(57) ABSTRACT

The insertion device is adapted to hold a high-frequency treatment tool for performing high-frequency current treatment, by means of a distal-end component of a flexible tube for insertion into lumens. The insertion device includes: a first indicator disposed on the front portion of the distal-end component; a first cover formed of an insulating elastoplastic material and covering the first indicator at the time of the prescribed attachment; an electrical insulation part as a second indicator disposed at the joint portion between the distal-end component and the flexible tube; and a second cover closely contacting the first cover and the electrical insulation part to apply an elastic force to each of them and covering the second indicator at the time of the prescribed attachment so that the leakage of high-frequency currents is prevented.

18 Claims, 6 Drawing Sheets

(51) Int. Cl.
  *G02B 23/24* (2006.01)
  *A61B 1/05* (2006.01)
  *A61B 1/06* (2006.01)
  *A61B 90/00* (2016.01)
  *A61B 1/07* (2006.01)
  *A61B 1/005* (2006.01)

(52) U.S. Cl.
  CPC ...... *A61B 1/00101* (2013.01); *A61B 1/00128* (2013.01); *A61B 1/00131* (2013.01); *A61B 1/00137* (2013.01); *A61B 1/018* (2013.01); *A61B 1/05* (2013.01); *A61B 1/0669* (2013.01); *A61B 1/07* (2013.01); *A61B 90/04* (2016.02); *G02B 23/2423* (2013.01); *G02B 23/2469* (2013.01); *A61B 1/0055* (2013.01); *A61B 1/00091* (2013.01); *A61B 1/00142* (2013.01); *A61B 1/0676* (2013.01); *A61B 2090/0481* (2016.02)

(58) Field of Classification Search
  CPC ............ A61B 1/00137; A61B 1/00142; A61B 1/0008; A61B 2090/0808; A61B 2090/0811
  See application file for complete search history.

(56) References Cited

U.S. PATENT DOCUMENTS

| | | | |
|---|---|---|---|
| 8,038,604 B2 * | 10/2011 | Hamazaki | A61B 1/0008 600/107 |
| 2012/0209167 A1 * | 8/2012 | Weber | A61B 17/3474 604/26 |
| 2016/0015253 A1 * | 1/2016 | Roop | A61B 1/00096 600/106 |

FOREIGN PATENT DOCUMENTS

| | | |
|---|---|---|
| JP | H09299316 A | 11/1997 |
| JP | H10216074 A | 8/1998 |

OTHER PUBLICATIONS

Japanese Office Action dated Aug. 1, 2017 in Japanese Patent Application No. 2017-522435.
English translation of International Preliminary Report on Patentability dated Jan. 11, 2018 together with the Written Opinion received in related International Application No. PCT/JP2016/067411.
Chinese Office Action dated Jan. 23, 2019 in Chinese Patent Application No. 201680037651.5.

\* cited by examiner

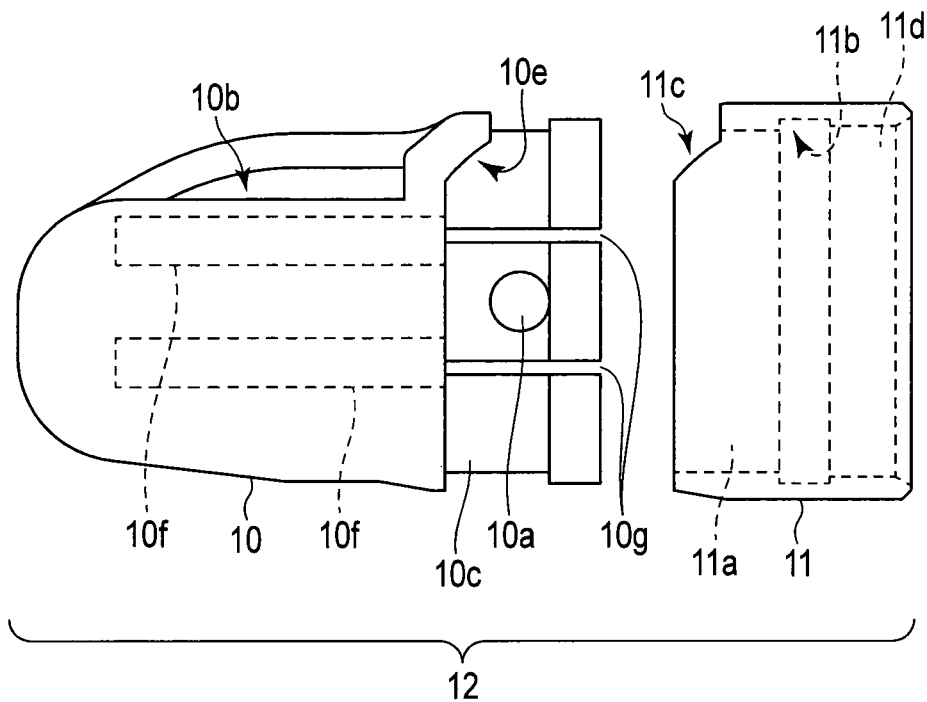
F I G. 2
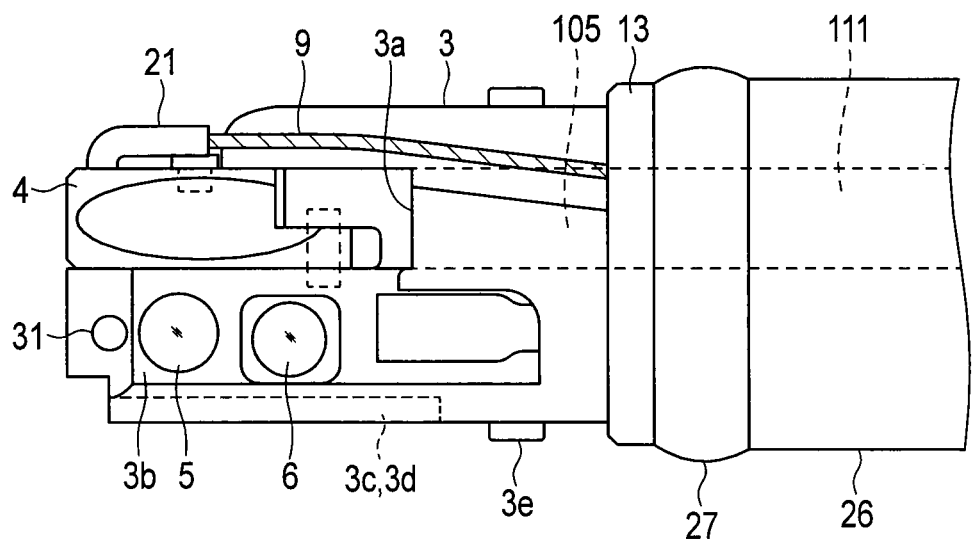
F I G. 3

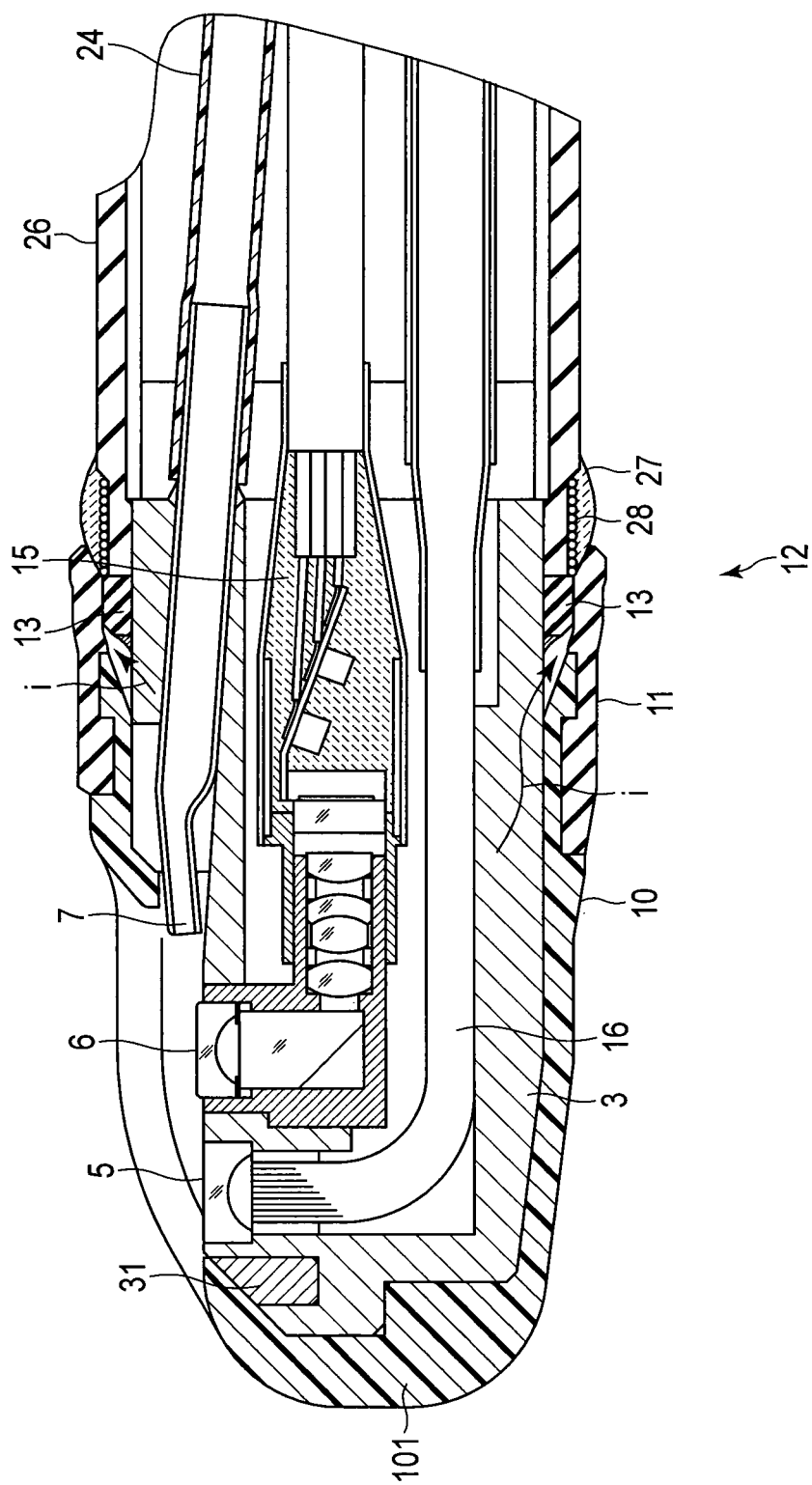
F I G. 8

DISTAL-END COVER, INSERTION DEVICE ATTACHED WITH DISTAL-END COVER, AND ENDOSCOPE INCLUDING INSERTION DEVICE

CROSS-REFERENCE TO RELATED APPLICATIONS

This is a Continuation Application of PCT Application No. PCT/JP2016/067411, filed Jun. 10, 2016, which was published under PCT Article 21(2) in Japanese.

This application is based upon and claims the benefit of priority from prior Japanese Patent Application No. 2015-131295, filed Jun. 30, 2015, the entire contents of which are incorporated herein by reference.

BACKGROUND OF THE INVENTION

1. Field of the Invention

The present invention relates to an insertion device including a distal-end cover that blocks high-frequency currents, and to an endoscope including the insertion device.

2. Description of the Related Art

A distal-end component is generally formed of a combination of multiple metal members. Thus, when an inserted high-frequency treatment tool is in contact with or near the metal members, these metal members may be used as part of the conveyance path for high-frequency currents or the feedback path for currents. As such, for inserting a high-frequency treatment tool into a living body's cavity, blocking measures must be taken to prevent high-frequency currents from being applied to living tissue other than treatment subjects. Such measures include attaching a distal-end cover to a distal-end component of an insertion device so that exposed metal members are covered. For example, Patent Document 1: Jpn. Pat. Appln. KOKAI Publication No. 09-299316 proposes a distal-end cover that is formed of electrically insulating materials into a cap shape for the attachment to a distal-end component of an insertion device.

Regarding the position to attach a distal-end cover, a distal-end component is provided with, in its proximal portion, an insulating part having a cylindrical, outwardly protruding flange. The distal-end cover is put to contact the flange of the insulating part for the attachment.

Generally, a distal-end cover attached to a distal-end component of an insertion device must be securely kept from being dropped within a body cavity. According to Patent Document 1, a distal-end cover is formed to have adjusted dimensions so that it has an inner diameter smaller than the outer diameter of a distal-end component. With such adjusted dimensions, the distal-end cover is deformed to expand when placed over the distal-end component, and makes a close contact due to an elastic force. Furthermore, the distal-end component is provided with a convex part around its periphery so that the distal-end cover under the elastic force is tightly engaged, and the fixing force is enhanced to provide a fall-off prevention structure.

The object of the present invention is to provide an insertion device which: enables easy attachment and secure engagement of a distal-end cover that blocks high-frequency currents and prevents current application, through the means including visual confirmation; shows good slipping properties when in a body cavity; and maintains a high safety in operations using high-frequency currents. Another object of the present invention is to provide an endoscope including the insertion device.

BRIEF SUMMARY OF THE INVENTION

According to an embodiment of the present invention, there is provided an insertion device comprising: a distal-end component at a distal end of a flexible tube for insertion into a lumen, the distal-end component adapted to hold an optical element for observation in the lumen; a circular electrical insulation part on a distal end of the flexible tube where the distal-end component is coupled, the electrical insulation part including a first color; an indicator at a distal portion of the distal-end component, the indicator including a second color; a first cover adapted to hide the indicator when attached over the distal-end component, the first cover including a third color different from the second color; and a second cover adapted to be integrally coupled to a proximal portion of the first cover and hide the electrical insulation part when the first cover is attached to the distal-end component, the second cover including a fourth color different from the first color.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 2 is a diagram showing an external structure of the distal-end cover, viewed from the side.

FIG. 3 is a diagram showing an external structure of the distal-end component without the distal-end cover, viewed from the above.

FIG. 8 is a diagram for explaining leakage of high-frequency currents in the distal-end component of the insertion device when the distal-end cover is attached.

DETAILED DESCRIPTION OF THE INVENTION

Embodiments of the present invention will be described in detail with reference to the accompanying drawings.

[First Embodiment]

Figure 1:
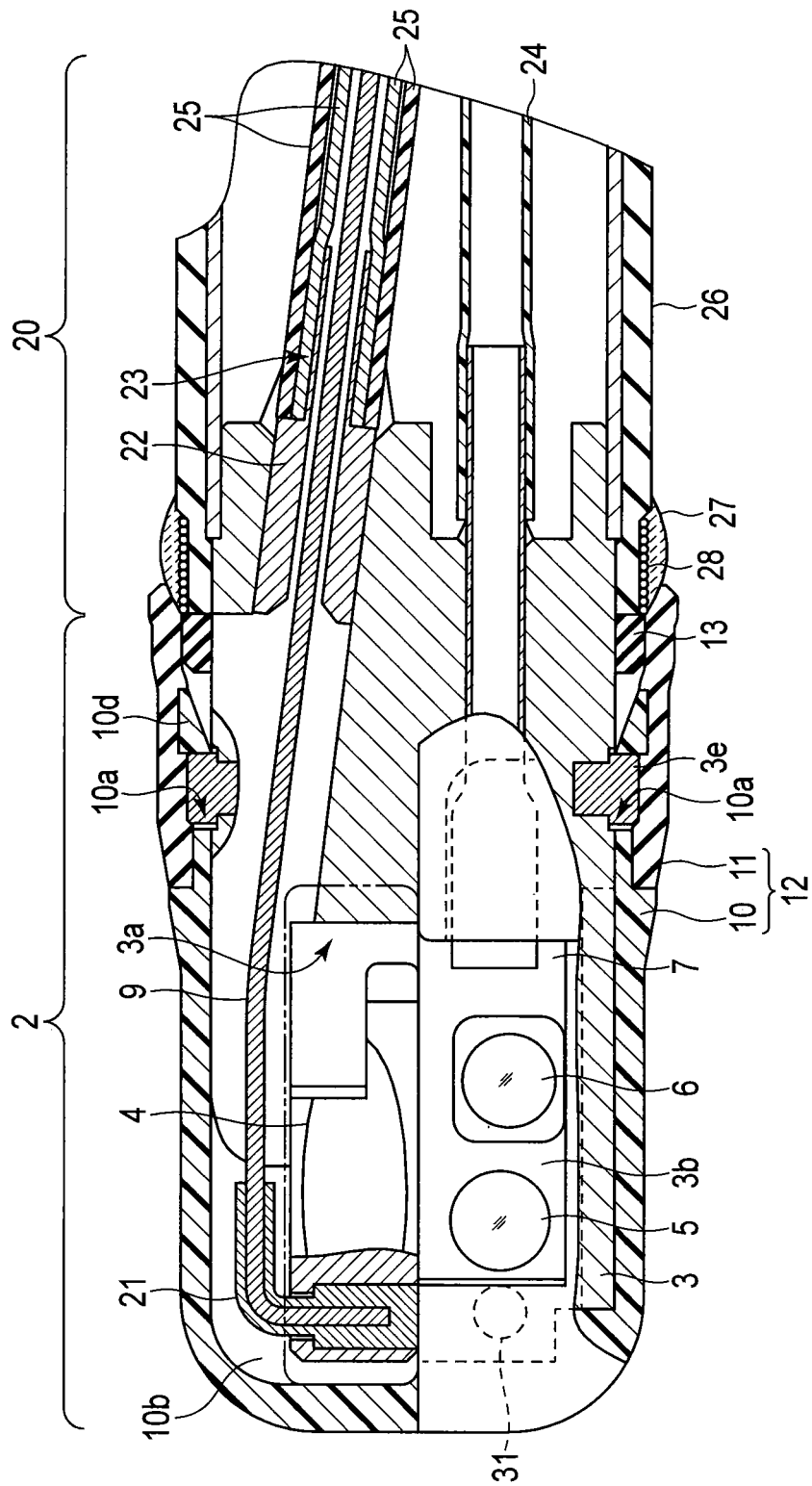
FIG. 1 is a sectional view from the above, showing a sectional structure of a distal-end component of an insertion device according to a first embodiment when a distal-end cover is attached.
Figure 4:
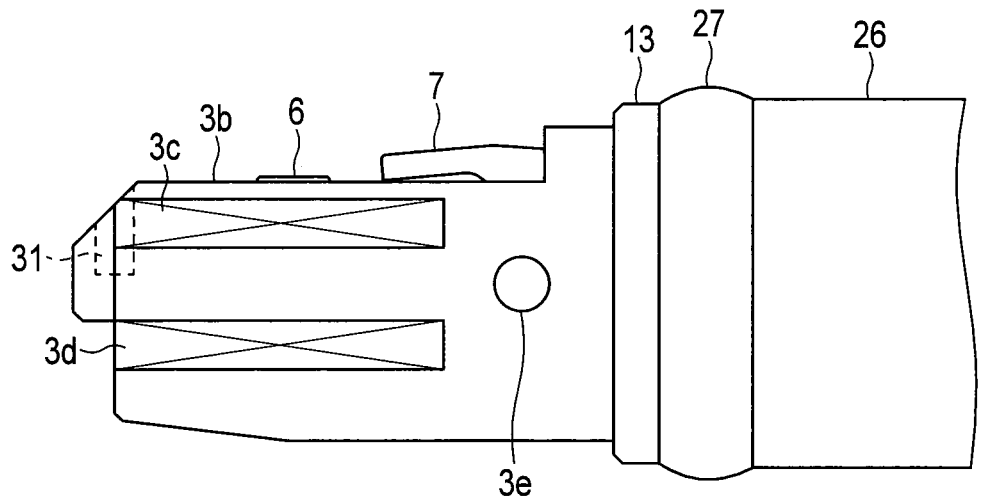
FIG. 4 is a diagram showing an external structure of the distal-end component without the distal-end cover, viewed from the side.
Figure 5:
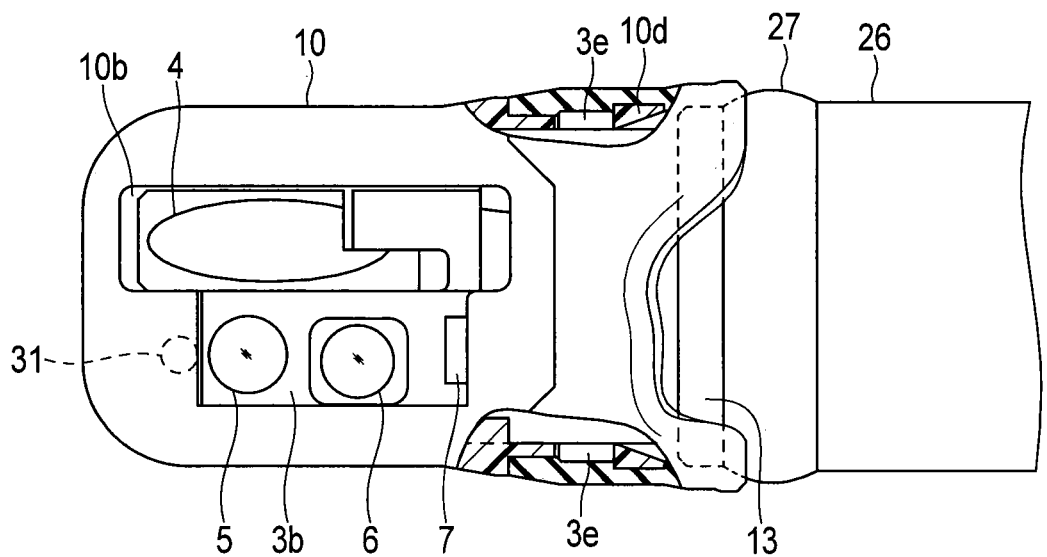
FIG. 5 is a diagram showing an external structure viewed from the above, when the distal-end cover is in a poor fit state on the proximal side.
Figure 6:
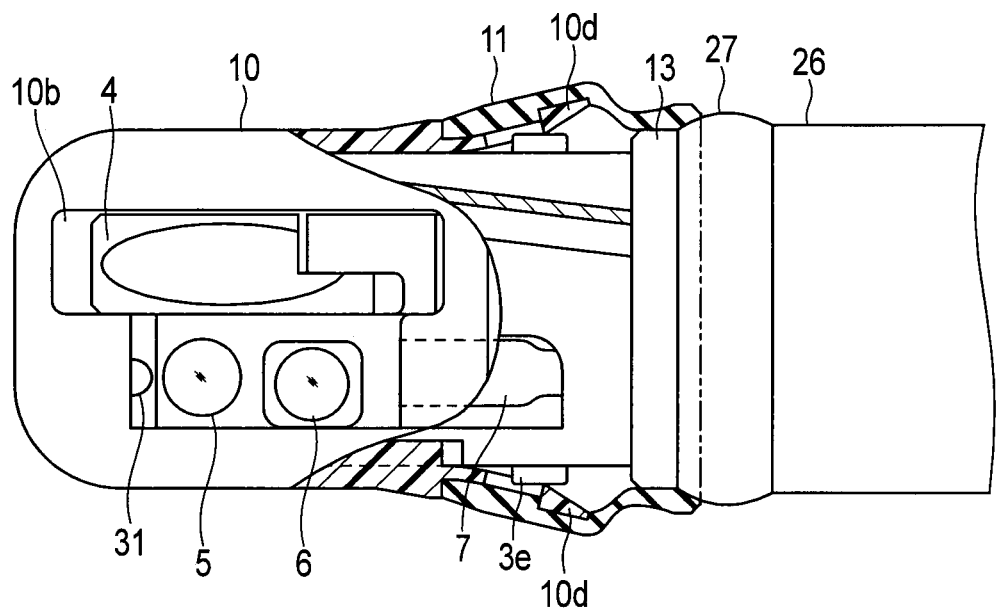
FIG. 6 is a diagram showing a sectional structure when the distal-end cover is in a poor fit state.
Figure 9:
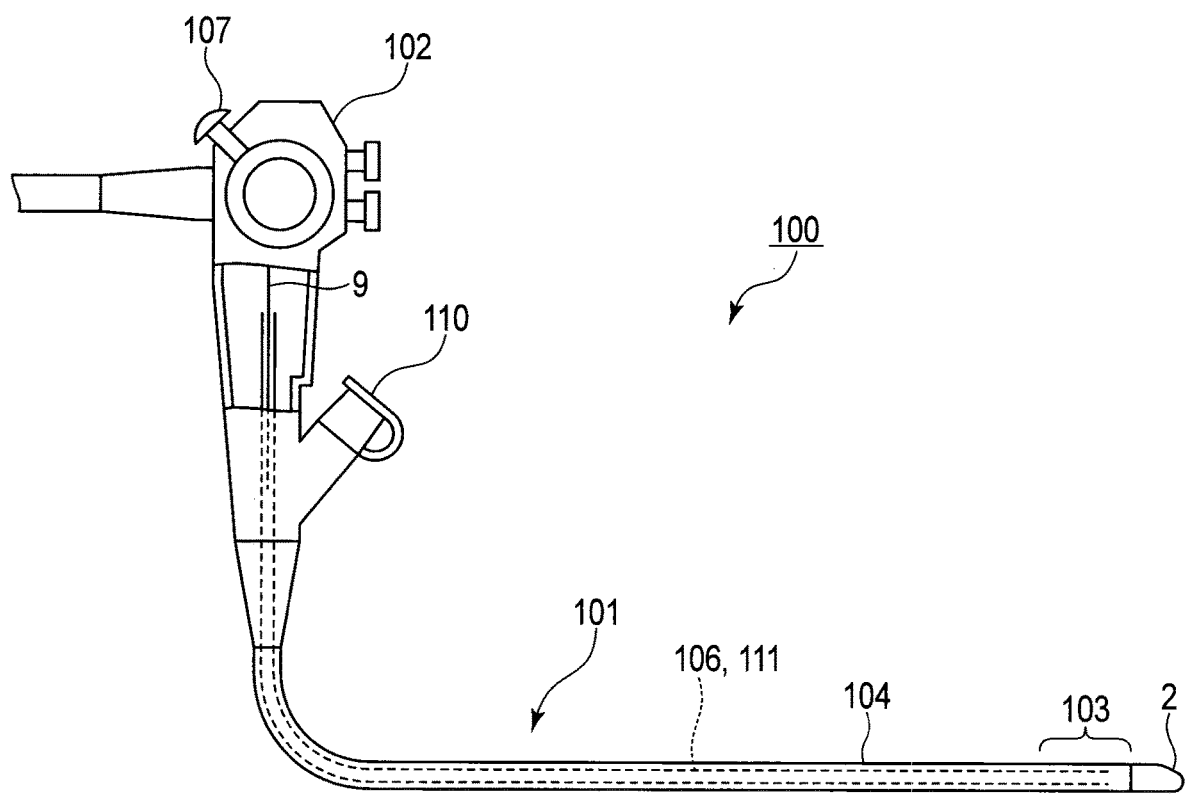
FIG. 9 is a diagram showing an example of the structure when the distal-end component of the insertion device is adopted in an endoscope.

FIG. 1 is a sectional view showing a distal-end component of an insertion device according to the first embodiment when a distal-end cover is attached. FIG. 2 shows the distal-end cover. FIG. 3 shows the distal-end component without the distal-end cover. FIG. 4 shows the distal-end component without the distal-end cover. FIG. 5 shows that the distal-end cover is in a poor fit state on the proximal side. FIG. 6 is a sectional view showing that the distal-end cover is in a poor fit state. FIG. 8 is a diagram for explaining leakage of high-frequency currents in the distal-end component with the distal-end cover attached. FIG. 9 shows one example of the structure when the distal-end component is applied to an insertion device of an endoscope.

In the following descriptions, a distal-end component of the insertion device of the endoscope shown in FIG. 9 will be used as an example of the distal-end component of the insertion device according to the embodiment.

For this distal-end component, a constructive example will be described, in which a swing base (or a raising base) to change the moving direction of an inserted high-frequency treatment tool is mounted. This swing base may be a swing mechanism that can change the moving direction not only in the vertical direction but also in the lateral direction crossing the vertical direction. The following embodiments will assume the treatment tool to be a high-frequency treatment tool, but this is not a limitation.

An endoscope 100 shown in FIG. 9 includes an insertion device 101 for insertion into a tubular cavity or a lumen, and an operation unit 102. The insertion device 101 is provided with, in its proximal portion, an insertion port (forceps port) 110 to insert a treatment tool that is adapted to perform electrical treatment, e.g., treatment using high-frequency currents, for treatment target sites. A cylindrical distal-end component 2 is arranged in the distal portion of the insertion device 101. The operation unit 102 is provided with a swing base operation unit 107. While not illustrated, it is assumed that this endoscope has a general system configuration including a light source device for supplying illumination light, a controller including a video processor for applying image processing to obtained image signals, a display for displaying observation images, a recorder for recording image signals, and so on.

The insertion device 101 is provided with, next to the distal-end component 2 and toward the proximal end, a bending part 103 and a flexible tube 104. The insertion device 101 includes a channel conduit 111 for a treatment tool to pass through, an air/water line 106 for supplying rinse liquids, air, or the like, and a long pull wire (pulling member) 9 for causing a swing movement (raising movement) of a swing base. Connections to the swing base operation unit 107 are established through this pull wire 9. Lever operations with the swing base operation unit 107 swing (turn) a swing base 4 to stand up or lie down.

The channel conduit 111 extends through the insertion device 101 from the insertion port 110 on the proximal side, and is connected to a treatment tool channel hole 105 (cf. FIG. 3). A channel opening 3a opens at the distal end. A high-frequency treatment tool is inserted from the insertion port 110, passes through the channel conduit 111, and comes out from the channel opening 3a of the treatment tool channel hole 105.

Next, the distal-end component 2 will be described with reference to FIGS. 1, 3, and 4.

This distal-end component 2 is generally constituted by a base member 3 formed of metal materials, such as stainless steel, the swing base 4 turnably provided to the base member 3, and a cylindrical distal-end cover 12. The base member 3 and a sheath 26 of the insertion device's distal portion 20 are fixed to each other by bonding fixation thin wires 28. The sheath 26 is a resin or rubber tube having insulation and water-tight properties. A fixation ring part 27 as a coating of an insulating resin material is formed to surround the surface of the fixation thin wires 28.

The base member 3 is divided into two parts along a longitudinal-axis direction, one of them including the channel opening 3a (cf. FIGS. 1 and 3) and the swing base 4 in front of the channel opening 3a, and the other including an observation surface 3b that is flatly formed with respect to the outer periphery. The channel opening 3a communicates with the insertion port 110 on the proximal side, through the channel conduit 111 for a treatment tool. Also, the observation surface 3b is provided with an illumination window part 5 for emitting illumination light guided through optical fiber 16 (cf. FIG. 8). Adjacent to the illumination window part 5, there is an observation window part 6 constituted by an imaging unit 15 [optical component]. The imaging unit 15 includes an optical system, imaging elements, electrical circuits, etc. (cf. FIG. 8). A nozzle 7 is disposed near the observation window part 6 in the longitudinally proximal portion. The nozzle 7 sprays rinse liquids, e.g., saline, and gases, e.g., air, supplied by an air/water line 24 (106) so that the illumination window part 5 and the observation window part 6 are rinsed as appropriate.

As shown in FIGS. 1, 3 and 8, there is a front indicator 31 [indicator or first indicator: second color] provided in such a manner that it is embedded in the distal end (foreside) of the distal-end component 2. The front indicator 31 has a color that differs at least from the exterior color of a first cover 10, and is preferably a prominent color such as those giving a complementary relationship in hue. It may be a black or white color. For use in rooms of weak illumination, it may adopt fluorescent colors or phosphorescent colors.

This embodiment assumes the front indicator 31 to be circular, but the front indicator 31 is not limited to a particular shape as long as it is easy to visually recognize. As will be described in detail later, the front indicator 31 is positioned so that it is hidden by the cover 12 when the attachment is established at a position prescribed with respect to the distal-end component 2 (prescribed position), as shown in FIG. 1 or 8. In the following descriptions, the prescribed position may suggest a position where the attachment between the distal-end cover 12 and the distal-end component 2 meets the attachment conditions to realize the prevention of dropping the distal-end cover according to a design specification. Also, the attachment at this prescribed position may be called prescribed attachment. The prescribed position in the context of this embodiment refers to an attachment position at which the front indicator 31 and a proximal indicator (insulation ring) 13 are both covered by the distal-end cover 12 and not visible, as will be described.

As shown in FIG. 4, groove-shaped rotation restricting parts 3c and 3d are formed at least on the side face of the base member 3 that is continuous to the observation surface 3b. The rotation restricting parts 3c and 3d extend in the longitudinal-axis direction in parallel with each other. The rotation restricting parts 3c and 3d restrict the distal-end cover 12 attached to the distal-end component 2 so that it does not rotate in the circumferential direction. Furthermore, a cylindrical locking pin 3e [locking member] is provided on each of the side faces, at a position more proximal than the rotation restricting parts 3c and 3d. The locking pin 3e fits a locking hole 10a in the later-described first cover 10 of the distal-end cover 12. The locking pin 3e is not limited to the cylindrical shape or any particular shape, as long as it projects to enable anchoring.

The swing base 4 includes a recessed contact face for contacting a treatment tool appearing out of the channel opening 3a to change its moving direction. The swing base 4 is provided with, at its outer face, a coupling part 21 to which the pull wire 9 is coupled. The pull wire 9 is connected to the swing base operation unit 107 through a wire guide member 25 fitted in a coupling member 23 that is fixed by a guide part 22. Responsive to lever operations, the pull wire 9 pushes and draws the coupling part 21, and the swing base 4 is raised or laid down in conjunction with the lever operations. Also, the insulation ring 13 [electrical insulation part], having insulation properties and functioning as a later-described proximal indicator [second indicator: first color], is provided around the entire periphery of the base member 3 so that it closely contacts the end faces of the sheath 26 and the fixation thin wires 28. This indicator will be described using a consistent reference symbol, and may be referred to as the proximal indicator 13. This insulation ring 13 is disposed on a more proximal side than the locking pin 3e and the locking hole 10a serving as a locking unit, that is, around the outer periphery of the joint between the distal-end component 2 and the flexible tube 104 (distal end of the bending part).

Next, the structure of the distal-end component 2 will be described with reference to FIGS. 1 and 2.

The distal-end cover 12 according to the embodiment is formed of two covers giving different effects and functions, i.e. the first cover 10 [third color different from the second color] and a second cover 11 [fourth color different from the first color]. Of these covers, the first cover 10 is of an insulating elasto-plastic resin material, e.g., plastics, and is injection-molded into a cylindrical cup shape having a closed end portion. The end portion adopts a curved shape, and the surface has a smoother surface roughness than rubber-made covers. Thus, the first cover 10 provides good slipping properties when in body cavities. The second cover 11 is of an insulating elastic material, e.g., rubber such as silicon rubber, or of an insulating elastic resin, etc., and is formed into a circular shape. Note that the insulating properties in the context of the embodiment are intended to provide effects of blocking high-frequency currents or preventing leakage.

The first cover 10 includes a window 10b for exposing the swing base 4, the illumination window part 5, and the observation window part 6 of the distal-end component 2 as an attachment target. In the following descriptions, the face where the window 10b opens will be assumed to be an upper face. Also, the direction from the distal end toward the proximal end (opening side) will be assumed to be a longitudinal direction, and the direction orthogonal to the longitudinal direction will be assumed to be a circumferential direction.

At the proximal portion of the first cover 10, a joint face 10c sunken from the outer peripheral face is formed around the periphery. At the opening-side end of the first cover 10, a fitting part 10d is provided. The fitting part 10d differs in level, i.e. has an increased thickness, to provide an engagement function. As shown in FIG. 1, the fitting part 10d is tapered so that its inner face expands toward the opening side, allowing the fitting part 10d to be easily placed over the base member 3 and reach beyond the locking pin 3e.

The circular locking hole (or circular groove) 10a is formed on both sides of the joint face 10c. The locking hole 10a engages with the locking pin 3e of the distal-end component 2 to contribute to drop prevention. Multiple linear slits 10g are formed on both sides of the joint face 10c. The slits 10g extend in the longitudinal direction, and are intended for elastically expanding the portions including the locking hole 10a outwardly when the cover is fitted to the distal-end component 2. Furthermore, multiple rotation preventing projections 10f are formed on the inner face of the first cover 10, which extends from the distal portion to the joint face 10c. The rotation preventing projections 10f are a plurality of bar-shaped projections (two in this example) adapted for engagement with the rotation restricting parts 3c and 3d.

The second cover 11 is of an insulating elastic material, such as rubber, and is formed into a circular shape. Its proximal contact face 11c coincides with a distal contact face 10e of the joint face 10c of the first cover 10, and its outer periphery is designed to be smoothly continuous with the outer periphery of the first cover 10.

The second cover 11 includes a joint face 11a formed in the distal-side inner peripheral face, which will make a close contact with the joint face 10c when fitted to the first cover 10. A fitting groove 11b for engagement with the fitting part 10d is formed on the proximal side, next to the joint face 11a. Also, the proximal-side inner peripheral face of the second cover 11 is formed as a joint face 11d designed to closely fit with the insulation ring 13 of the distal-end component 2.

The second cover 11 is designed so that it exerts, when fitted to the first cover 10 and the insulation ring 13, an inward elastic force to each component. This elastic force can be realized by, for example, forming the inner diameter of the second cover 11 to be smaller than the outer diameters of the first cover 10 and the distal-end component 2. Also, the first cover 10 and the second cover 11 may be bonded together by applying an adhesive (silicon-based or epoxy-based adhesive, etc.) to the joint face 10c and the distal contact face 10e, and/or to the joint face 11a and the proximal contact face 11c. The positions to apply the adhesive are not limited to particular positions, but may be any positions where the covers mutually contact.

In addition, the embodiment is not limited to the foregoing size relationships, the bonding sites, or the types of adhesives for use, as long as the locking pin 3e of the distal-end component 2 and the locking hole 10a of the distal-end cover 12 are urged in the locking direction (inward direction) by the second cover 11 upon the attachment of the distal-end cover 12 to the distal-end component 2. The embodiment is not limited to the above as long as a body fluid that has passed through the distal contact face 10e (proximal contact face 11c), which is a boundary between the first cover 10 and the second cover 11, and pooled at a raising-base housing does not leak out of the distal-end cover 12 during the attachment.

Next, descriptions will be given of the leakage of high-frequency currents in the distal-end component 2, with reference to FIG. 8.

A high-frequency treatment tool extends inside the insertion device 101 from the insertion port 110 shown in FIG. 9, and exits from the channel opening 3a of the distal-end component 2. When a high-frequency current is applied to the high-frequency treatment tool to perform treatment, a high-frequency current i would also flow in the distal-end component 2, as the high frequency can propagate through space. In this instance, since the second cover 11 and the insulation ring 13 are in close contact with each other, the high-frequency current i does not leak out from the closely contacted portion to flow out of the distal-end cover 12. That is, the high-frequency current i does not leak out from the portion that is not visible to an operator, such as the back of the distal-end cover 12. Thus, even if the distal-end cover 12 contacts the living tissue other than a treatment subject in a body cavity, the possibility of causing damage, such as burns, can be greatly reduced. Also, since the first cover 10 and the second cover 11 closely contact each other without a gap in their boundary, the high-frequency current does not leak out of the distal-end cover 12 through this boundary, either.

Steps to attach the first cover 10 and the second cover 11 to the distal-end component 2, as well as the effects and functions will be described with reference to FIGS. 1, 5, and 6.

First, the second cover 11 is slid over the first cover 10 from the proximal side until the proximal contact face 11c and the distal contact face 10e abut onto each other. The joint face 10c and the joint face lie are brought into close contact with each other, and the fitting part 10d is engaged with the fitting groove 11b, so that the first cover 10 and the second cover 11 are united as the distal-end cover 12.

Next, the distal-end cover 12 is placed over the distal-end component 2, and slid to the proper position where the joint face 11d of the second cover 11 has gone across the insulation ring 13 and is engaged with the fixation ring part 27. At this time, the first cover 10 is moved forward, with the rotation preventing projections 10f inserted into the rotation restricting parts 3c and 3d. The locking pin 3e of the distal-end component 2 is fitted into the locking hole 10a.

In this fitting step, when the proper attachment position of the first cover 10 has been reached as shown in FIG. 5, the front indicator 31 is covered by the first cover 10 so that it becomes not visible from outside. On the other hand, if the front indicator 31 is visible through the window 10b as shown in FIG. 6, it is suggested that the cover is not placed up to the prescribed position. The possible state that can be assumed in this case is that the fitting part 10d is on the locking pin 3e or that the fitting part 10d stays before the locking pin 3e. If the fitting part 10d is on the locking pin 3e, the poor attachment is visually and haptically easy to recognize. In other words, once the front indicator 31 becomes not visible, it can be determined that the first cover is placed up to the prescribed position.

Conventionally, attaching operations were terminated after empirically or intuitively determining the placement of a cover up to a prescribed position. According to the present embodiment, the attachment at the prescribed position is determined upon sliding the cover until the front indicator 31 is not visible, while visually checking.

The second cover 11 is determined to be attached at the prescribed position when it has been placed over the distal-end component 2 integrally with the first cover 10 to cover the proximal indicator 13 as an insulation ring. On the other hand, when part of the proximal portion of the second cover 11 does not reach the proximal indicator 13, the proximal indicator 13 is partially exposed as shown in FIG. 5. In this case, even if only a portion of the proximal indicator 13 is exposed, it is determined that the base member 3 is also exposed or has a space with the second cover 11, and that the cover is therefore not placed up to the prescribed position.

In this embodiment, the indicators are covered by the distal-end cover 12 for determination of the attachment at the prescribed position. However, from the opposite viewpoint, the indicators may be disposed at the positions that will be exposed when the distal-end cover 12 has been properly attached. For example, the indicators may be disposed at multiple positions near the frame of the window 10b of the first cover 10 so that the attachment at the proper position is determined when the window 10b comes to the correct position. Also, in the second cover 11, multiple through-holes may be provided at the proximal portion that closely contacts the fixation ring part 27. The fixation ring part 27 may be provided with indicators at the positions that overlap the through-holes upon establishment of the proper attachment. Thus, if the indicators are visible through these through-holes when the distal-end cover 12 is attached, it can be determined that the cover is attached at the proper position.

In this embodiment, the first cover 10 and the second cover 11 are prepared by separate production steps and fitted together to form the integral distal-end cover 12. However, the distal-end cover 12 is not limited to such a structure. The distal-end cover 12 may be integrally produced by continuous production steps. For example, of the injection-molding production techniques, dissimilar-material molding, i.e., so-called two-color molding, may be adopted. According to this production method, a plastic material is first injected into a primary cavity to mold the first cover 10 as a primary mold. Subsequently, the first mold is put in a secondary cavity and a rubber material is injected to integrally mold the second cover 11 coupled to the first cover 10. With this production method, the distal-end cover 12 may be integrally produced.

The descriptions of the embodiment have assumed a constructive example where the distal-end component 2 is provided with the locking pin 3e, and the first cover 10 is provided with the locking hole 10a for the locking pin 3e to fit. However, the embodiment is not necessarily limited to this structure. For example, the first cover 10 may be provided with the locking pin 3e, and the distal-end component 2 may be provided with a locking hole for the locking pin 3e to fit. That is, as long as the distal-end component 2 and the first cover 10 are anchored by each other through uneven structural portions, an anchoring structure in which the first cover 10 is provided with a protruding member and the distal-end component 2 (base member 3) is provided with a recessed member may be adopted.

The distal-end cover 12 according to the foregoing embodiment is constituted by the first cover 10 and the second cover 11 each having insulation properties. The distal-end cover 12, can be attached, while realizing a complete coverage from the tip end of the base member 3 of the distal-end component 2 to the insulation ring 13, except the window 10b.

The first cover 10 is formed of a plastic resin or plastics, etc., and has a finer surface roughness and a smaller frictional force than elastic members formed of rubber, etc. Thus, the first cover 10 provides good slipping properties and superior operability when in body cavities. Also, the second cover 11 formed of an elastic member is attached in such a manner that it exerts an elastic force to urge the first cover 10 against the distal-end component 2 to establish a close contact across the first cover 10 to the insulation ring 13 of the distal-end component 2. Therefore, high-frequency currents can be prevented from leaking, not only from the portion covered by the first cover 10, but also from the proximal end of the second cover 11, i.e., the proximal end of the distal-end cover 12. Moreover, the second cover 11 covers and exerts the elastic force to the locked positions of the first cover 10 from outside, and therefore, it can prevent the first cover 10 from dropping from the distal-end component 2. In addition, since the second cover 11 arranged on the proximal portion of the distal-end component 2 has a narrower width than the first cover 10 arranged on the distal portion of the distal-end component 2, an increase of the frictional force can be suppressed.

The distal-end component 2 is provided with the indicators at the front side (distal side) and the proximal side so that the prescribed position for attachment is indicated for each of the first cover 10 and the second cover 11. Therefore, the determination of the proper attachment can be assured by visual confirmation, without intuitive judgment. If the indicators are absent, a person other than the one who actually attached a distal-end cover is required to directly touch the distal-end cover by hand in order to confirm the attachment state. According to the embodiment, the attachment state can be visually confirmed, and therefore, occasions of unnecessary touching can be reduced, contributing to the prevention of inadvertent contamination.

[Modification Example of First Embodiment]

Figure 7:
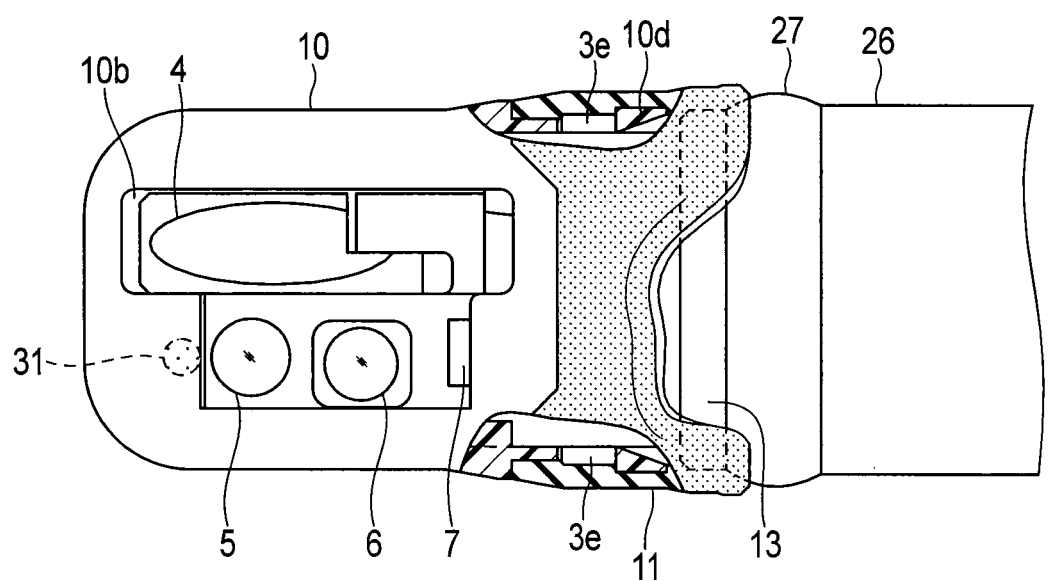
FIG. 7 is a diagram showing a structure as a modification example, which is capable of distinguishing a poor fit state of the distal-end cover by colors.

FIG. 7 is a diagram showing a structure capable of distinguishing a poor fit state of the distal-end cover by color, as a modification example of the first embodiment.

This modification example allows for easier visual confirmation using "black" or "white" coloring for each member in the combination of the front indicator 31, the first cover 10, the second cover 11, and the insulation-ring proximal indicator 13. In this example, the exterior of the first cover 10 is colored white, and the front indicator 31 is colored black. Contrary to this, the exterior of the second cover 11 is colored black, and the proximal indicator 13 is colored white. By differentiating colors in this manner, it is possible to facilitate visual confirmation of the attachment state even in the corners of a surgical room, where the illumination intensity is weak unlike in the area of a surgical bed.

When colors other than black and white are used, colors standing out from each other, for example, colors giving a complementary relationship in hue are preferable. If the use in dim rooms is expected, fluorescent colors or phosphorescent colors may be adopted.

It is preferred that the distal-end cover in the foregoing embodiments assumes a single use, e.g., it is designed to be disposable. In that case, the distal-end cover and the distal-end component 2 in each embodiment preferably have a structure that enables the detachment of the distal-end cover from the distal-end component 2 by permitting the anchoring portion therebetween to be broken to release them.

With such a structure, a single use of the distal-end cover in each embodiment can be guaranteed for each treatment case of the endoscope 100 so that hygiene aspects are improved. Also, the endoscope 100, especially the areas surrounding the swing base 4, can be easily cleaned after the use in each treatment case. Thus, the safety can be further enhanced.

According to the present invention, it is possible to provide an insertion device which: enables easy attachment and secure engagement of a distal-end cover that blocks high-frequency currents and prevents current application, through the means including visual confirmation; shows good slipping properties when in a body cavity; and maintains a high safety in operations using high-frequency currents. According to the present invention, it is also possible to provide an endoscope including the insertion device.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

The invention claimed is:

1. An insertion device comprising:
a distal-end component at a distal end of a flexible tube for insertion into a lumen, the distal-end component being configured to hold an optical element for observation in the lumen;
a circular electrical insulation part on a more distal end than the flexible tube, the electrical insulation part including a first color;
an indicator at the distal-end component, the indicator including a second color;
a first cover adapted to be attached over the distal-end component, wherein the first cover hides all portions of the indicator in a first state when the first cover is attached at a first prescribed position and the first cover does not hide at least a portion of the indicator in a second state when the first cover is not attached at the first prescribed position, the first cover including a third color different from the second color; and
a second cover adapted to be coupled to a proximal portion of the first cover attached to the distal-end component, wherein the second cover hides all portions of the electrical insulation part in a third state when the second cover is attached at a second prescribed position and the second cover does not hide at least a portion of the electrical insulation part in a fourth state when the second cover is not attached at the second prescribed position, the second cover including a fourth color different from the first color,
wherein the first cover has a finer surface roughness than the second cover, and
the second cover has a higher elasticity than the first cover.

2. The insertion device of claim 1, wherein
the first color of the electrical insulation part is equal to the second color of the indicator, and
the third color of the first cover is equal to the fourth color of the second cover.

3. The insertion device of claim 2, wherein a part of the first cover that hides the indicator includes the third color.

4. The insertion device of claim 1, wherein the first cover and the second cover comprise an electrically insulating material to prevent electrical conduction between the distal-end component and an outside.

5. The insertion device of claim 1, further comprising an opening to optically expose the optical element for observation in the lumen, wherein
the indicator is positioned in the distal-end component so that when the first cover is attached to the distal-end component, the indicator is located adjacent the opening.

6. The insertion device of claim 1, wherein the first cover is fixed to a position defined in an exterior of the distal-end component via a locking unit between the distal-end component and the first cover.

7. The insertion device of claim 6, wherein, in the prescribed position, the first cover is attached to the distal-end component in a state that the first cover is prevented from dropping from the distal-end component.

8. The insertion device of claim 1, wherein the distal-end component comprises a treatment-tool conduit for a treatment tool to pass through, the treatment tool being configured to apply an electrical current.

9. The insertion device of claim 8, wherein
the distal-end component comprises a treatment-tool swing base configured to swing an end portion of the treatment tool, and
the first cover comprises a cutout from which the end portion of the treatment tool comes out.

10. The insertion device of claim 1, wherein the first cover and the second cover are adapted to be attachable and detachable to the distal-end component.

11. The insertion device of claim 1, wherein the first cover and the second cover are separate members.

12. The insertion device of claim 11, wherein the second cover is shorter than the first cover in a longitudinal direction.

13. The insertion device of claim 11, wherein
the first cover comprises an outer peripheral surface, the outer peripheral surface including the proximal portion having a first joint surface, the first joint surface extending in a longitudinal direction and being offset in an inwardly radial direction from the outer peripheral surface, and
the second cover comprises an inner peripheral surface, the inner peripheral surface including a distal portion having a second joint surface, the second joint surface extending in a longitudinal direction and being offset in an outwardly radial direction from the inner peripheral surface, the second joint surface being configured to couple with the first joint face.

14. The insertion device of claim 11, wherein the first cover comprises a slit in the proximal portion.

15. The insertion device of claim 1, further comprising a locking unit between the distal-end component and the first cover, the locking unit being configured to fix the first cover to a position defined in an exterior of the distal-end component,
wherein the locking unit comprises a projecting locking pin and a recessed locking hole configured to couple to each other.

16. An endoscope comprising the insertion device of claim 1, as an insertion unit to be inserted into the lumen.

17. A distal-end cover for use with an endoscope,
the endoscope comprising:
a distal-end component at a distal end of a flexible tube for insertion into a lumen, the distal-end component adapted to hold an optical element for observation in the lumen;
a circular electrical insulation part on a more distal end than the flexible tube, the electrical insulation part including a first color; and
an indicator at the distal-end component, the indicator including a second color,
wherein the distal-end cover is adapted to be attached to the distal-end component of the endoscope, and the distal-end cover comprises:
a first cover adapted to be attached over the distal-end component, wherein the first cover hides all portions of the indicator in a first state when the first cover is attached at a first prescribed position and the first cover does not hide at least a portion of the indicator in a second state when the first cover is not attached at the first prescribed position, the first cover including a third color different from the second color; and
a second cover adapted to be coupled to a proximal portion of the first cover attached to the distal-end component, wherein the second cover hides the all portions of the electrical insulation part in a third state when the second cover is attached at a second prescribed position and the second cover does not hide at least a portion of the electrical insulation part in a fourth state when the second cover is not attached at the second prescribed position, the second cover including a fourth color different from the first color,
wherein the first cover has a finer surface roughness than the second cover, and
the second cover has a higher elasticity than the first cover.

18. An insertion device comprising:
a distal-end component at a distal end of a flexible tube for insertion into a lumen, the distal-end component adapted to hold an optical element for observation in the lumen;
a circular electrical insulation part on a more distal end than the flexible tube, the electrical insulation part including a first color;
an indicator at the distal-end component, the indicator including a second color;
a cover adapted to be attached over the distal-end component, the cover comprising a first cover and a second cover coupled to a proximal portion of the first cover,
wherein the cover hides all portions of the indicator and the electrical insulation part in a first state when the cover is attached at a prescribed position and the cover does not hide at least a portion of one or more of the indicator and the electrical insulation part in a second state when the cover is not attached at the prescribed position, the first cover including a third color different from the second color, the second cover including a fourth color different from the first color; and
wherein the first cover has a finer surface roughness than the second cover, and
the second cover has a higher elasticity than the first cover.

* * * * *